United States Patent [19]

Shaber et al.

[11] Patent Number: 5,451,563
[45] Date of Patent: Sep. 19, 1995

[54] SILYL HETEROCYCLIC FUNGICIDES

[75] Inventors: Steven H. Shaber, Horsham; Edward M. Szapacs, Center Valley; Reynolds Charles H., Lansdale, all of Pa.

[73] Assignee: Rohm and Haas Company, Philadelphia, Pa.

[21] Appl. No.: 213,771

[22] Filed: Mar. 16, 1994

[51] Int. Cl.$^6$ .................... A01N 43/40; A01N 43/54; C07F 7/02
[52] U.S. Cl. ..................... 504/193; 504/150; 504/235; 504/236; 504/239; 504/251; 544/225; 544/229; 546/2; 546/14
[58] Field of Search ............. 504/190, 193, 235, 236, 504/239, 251; 544/225, 229; 546/2, 14

[56] References Cited

U.S. PATENT DOCUMENTS

| | | | |
|---|---|---|---|
| 4,510,136 | 4/1985 | Moberg | 514/63 |
| 4,530,922 | 7/1985 | Moberg | 514/63 |

FOREIGN PATENT DOCUMENTS

| | | |
|---|---|---|
| 8802178 | 3/1987 | Australia . |
| 241429 | 10/1987 | European Pat. Off. . |
| 8911159 | of 0000 | Japan . |

OTHER PUBLICATIONS

Aukenthaler et al, "Preparation and testing of Alkyl Methylsilanes as Agrochemical Fungicides", CA 112; 56271u, (1990).

Agrarchemickalien, "Preparation of Azomethylsilanes as Agrochemical Fungicides", CA 113; 59527g, (1990). Tamao et al., "Nickel—Phosphine Complex Grinard Coupling."Tetrahedron, vol. 38, No. 22, pp. 3347–3354, (1982).
Fisher et al., "Rates of Base-Catalysed Cleavage of ..., Trimethylsilanes, "Journal of Organometallic Chemistry, 136, pp. 323–332 (1977).
Anderson et al., "The Solvolysis of 2-trimethylsilypyridine by Alcohols and Water, "J. Chem. Soc. (B), pp. 450–452 (1988).

*Primary Examiner*—Ceila Chang
*Attorney, Agent, or Firm*—Joseph F. Leightner

[57] ABSTRACT

Fungicidal heterocyclic silyl compounds of the general formula

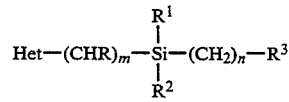

have been discovered wherein Het is a six membered heterocyclic moiety; R is hydrogen or a trisubstituted silyl group; $R^1$, $R^2$ and $R^3$ are independently selected from substituted or unsubstituted alkyl, alkenyl, alkynyl, aryl, arylalkyl or pyridyl groups; m is 0 or 1 and n is zero, one or two.

16 Claims, No Drawings

SILYL HETEROCYCLIC FUNGICIDES

BACKGROUND OF THE INVENTION

1. Field of the Invention

This invention relates to silyl heterocyclic compounds useful as broad spectrum fungicides.

2. Description of the Prior Art

Silyl heterocyclic compounds have been disclosed in the literature.

J. Organometallic Chem. 136, 323-332 (1977) discloses the synthesis of 2-, 3- and 4-trimethylsilylpyridine and 2-, 3-, and 4-(trimethylsilylmethyl) pyridine. J. Chem. Soc. B 4, 450-452 (1968) describes the synthesis of 2-, 3- and 4-trimethylsilylpyridine.

Tetrahedron 38 No. 22, 2347-2354 (1982) reports the synthesis of 3-(trimethylsilylmethyl) pyridine. None of the above references describes or suggests the fungicidal use of these heterocyclic compounds.

JP02990883 reports the synthesis and fungicidal use of certain 5-(trisubstitutedsilyl) pyrimidines.

Carvon et al., European Patent Application 0 313 353 A1, Apr. 26, 1989, describes aryl substituted morpholinyl silanes which are useful as agricultural fungicides.

Summary of the Invention

This invention relates to fungicidal compounds of the general formula

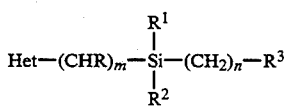   I wherein Het is a six member heterocyclic ring containing 1 or 2 nitrogen atoms and 4 or 5 carbon atoms; R is H or $Si(R^1)(R^2)(R^3)$; $R^1$, $R^2$ and $R^3$ are independently selected from the group consisting of ($C_1$-$C_6$) alkyl, ($C_2$-$C_6$) alkenyl, ($C_2$-$C_6$) alkynyl, ($C_1$-$C_6$) alkoxy, optionally substituted aryl, such as phenyl and pyridyl, optionally substituted aralkyl, such as benzyl and phenethyl each of which may be optionally substituted with up to three substituents wherein the substituents may be the same or different substituents selected from ($C_1$-$C_6$) alkyl, ($C_2$-$C_6$) alkenyl, ($C_2$-$C_6$) alkynyl, ($C_1$-$C_6$) alkoxy, halo or cyano, m is 0 or 1, n is 0, 1 or 2 and the agronomically acceptable enantiomorphs, acid addition salts and metal complexes thereof with the proviso that when $R^1=R^2=R^3$ is methyl Het is not pyridine, and when $R^1$ is ($C_1$-$C_6$)alkyl or $CH_2=CH_2$, $R^2$, $R^3$ is methyl or optionally substituted phenyl and m=n=0, Het is not pyrimidine.

A preferred embodiment are compounds, salts and enantiomorphs represented by formula I wherein Het is pyridyl, pyrimidyl or pyrazinyl and $R^1$, $R^2$ and $R^3$ are the same or different radical selected from methyl, phenyl, benzyl or phenethyl.

In yet another aspect, this invention relates to a method of controlling fungi comprising contacting said fungi or the locus of said fungi with a fungicidally effective amount of a compound of Formula I.

DETAILED DESCRIPTION OF THE INVENTION

The term "aryl" as used in the present specification defines an aromatic ring structure of 6 to 10 carbon atoms, preferably a phenyl or napthyl group which may be unsubstituted or optionally substituted with up to 3 substituents, preferably with 1 substituent, such as halo, nitro, cyano, ($C_1$-$C_{12}$) alkyl, ($C_3$-$C_8$) cycloalkyl, ($C_1$-$C_{12}$) haloalkyl, ($C_1$-$C_{12}$) alkoxy, ($C_2$-$C_{12}$) alkenyl, ($C_3$-$C_8$) cycloalkenyl, ($C_2$-$C_{12}$) alkynyl, ($C_5$-$C_8$) cycloalkynyl, ($C_1$-$C_{12}$) alkylthio, ($C_1$-$C_{12}$) alkylsulfinyl, ($C_1$-$C_{12}$) alkylsulfonyl, phenyl, phen ($C_1$-$C_{12}$) alkyl, phen ($C_2$-$C_{12}$) alkenyl, phen ($C_2$-$C_{12}$) alkynyl or ($C_5$-$C_6$) cycloalkyl ($C_1$-$C_6$) alkyl.

Typical aryl groups encompassed by this invention are phenyl, naphthyl, 2, 4-dichlorophenyl, 4-methylphenyl, 4-methoxyphenyl, 4-nitrophenyl, 4-fluorophenyl, 4-chlorophenyl, 4-trifluoromethylphenyl, 4-bromophenyl, 3-chlorophenyl, 3-fluorophenyl, 4-bromophenyl, 4-phenyl, 2-fluorophenyl, 2-chlorophenyl, 2-cyanonaphthyl, 4-chloronaphthyl and 4-mercaptiomethylphenyl.

The term "Het" as used in the present specification defines a 6-member heterocyclic ring consisting of 4 or 5 carbon atoms and 1 or 2 nitrogen atoms. As used herein Het is understood to be unsubstituted, i.e., all of the carbon atoms which do not form the linkage to the molecule contain only hydrogen atoms. Examples of heterocyclic rings encompassed by this invention are 2-pyridyl, 3-pyridyl, 4-pyridyl, 2-pyrimidyl, 4-pyrimidyl, 5-pyrimidyl, pyrazinyl, 3-pyridazinyl, and 4-pyridazinyl.

The term "alkyl" as used in the present specification defines both straight and branched carbon chains containing from 1 to 6 carbon atoms.

The term "aralkyl" as used in the present specification defines a group where in the alkyl chain is from 1 to 5 carbon atoms and can be branched or straight chained, preferably the latter, and the aryl portion is defined as above. Typical aralkyl substituents include, but are not limited to 2,4-dichlorobenzyl, 4-chlorobenzyl, 2,4-dibromobenzyl, 4-bromobenzyl, 4-fluorobenzyl, 2,4,6-trichlorobenzyl, 3,5-dimethoxyphenethyl, 4-chlorophenethyl, 4-methylphenethyl, 2,4-dichlorophenethyl, 2,4,5-trimethylphenbutyl and the like.

The term "fungicidally effective amount" means a quantity of compound which causes a reduction of the pest or fungus population or decreases crop damage as compared to a control group.

The term "agronomically acceptable carrier" means a solid or liquid which is biologically, chemically, and physically compatible with the compounds of this invention.

The compounds of this invention may be prepared by several synthetic methods as illustrated below.

Procedure A

Procedure B

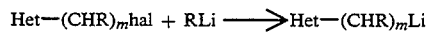

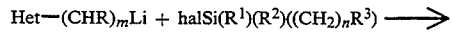

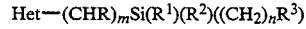

Procedure C

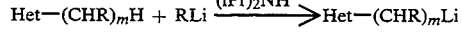

-continued

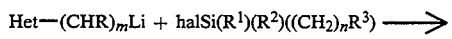

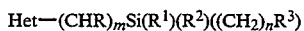

Procedure D

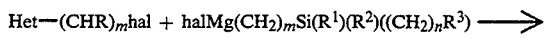

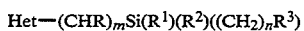

Het, $R$, $R^1$, $R^2$, $R^3$ m and n are as described above; hal is bromo or chloro; and iPr is isopropyl.

Procedure A involves the preparation of the heterocyclic Grignard reagent followed by reaction with the appropriate halosilane. The first reaction is conveniently carried out in refluxing diethyl ether, but other solvents and temperatures may be selected from standard procedures in the chemical literature. This procedure is preferred when the haloheterocycle is a bromoheterocycle and m is 0.

Procedure A, the reaction of 2-chloropyridine and 3-bromopyridine with trimethylsilyl chloride is described in J. Organometallic Chem. 136, 323–332 (1977) and Liebigs Ann. Chem. 6, 842–857 (1979)

Procedure B is illustrated by the reaction of a lithioheterocycle with the appropriate halosilane at temperatures of from about −100° C. to −50° C., preferably about −78° C. in an inert solvent. The reaction is especially preferred when halo is bromo and m is 0. Procedure B, the reaction of 3- and 4- bromopyridines with trimethyl silyl chloride is described in J. Chem. Soc. B, 4, 450–452 (1968)

Procedure C is particularly useful when n is 1. It involves deprotonation of heterocyclic methyl groups by lithium diisopropyl amide prepared from phenyl lithium and diisopropyl amine. The deprotonated methyl heterocycle is then reacted with the appropriately substituted halosilane at temperatures of from about −100° C. to −50° C., preferably about −78° C. in an inert solvent. This procedure has been used to react 2, 3 and 4- picolines with trimethyl silyl chloride and is described in J. Organometallic Chem. 136, 323–332 (1977)

Procedure D is accomplished by coupling the Grignard reagent of silylmethyl halide with haloheterocycles in diethyl ether using the catalyst $NiCl_2dppp$ ($NiCl_2Ar_2P(CH_2)_2 PAr_2$). This procedure is preferred when m is 1 and the haloheterocycle is a bromoheterocycle. Procedure D for the reaction between 3-bromopyridine and trimethylsilyl methyl magnesium chloride is described in Tetrahedron, 38 (22), 3347–3354 (1982).

The starting material for the preparation of the silyl heterocycles of this invention, $halSiR^1R^2(CH_2)_n)R^3$), are commercially available or can be prepared via known procedures from dihalodisubstituted silanes. When n is 2, the starting halosilane, $halSiR^1R^2(CH_2)_2R^3$ is preferably prepared from $halSiR^1R^2H$ and an olefin, $CH_2=CHR^3$, in the presence of $H_2PtCl_6$ and is described in Journal of Organic Chemistry, 29, 2519–2524, 1964.

It will be recognized that the silyl heterocycles of this invention may in certain cases exist in different optical isomeric forms. This invention is intended to include all such enantiomorphs. Likewise, the compounds of this invention may be converted into acid addition salts and metal complexes by standard chemical procedures. These acid addition salts and metal complexes are within the scope of this invention

EXAMPLES

The following examples in Table 1 are provided merely as illustrations and are not to be considered as limitations or restrictions of the scope of this invention. $R^1$, $R^2$, $R^3$, m, n and Het are defined as in Formula I. The Procedure is A, B, C or D as defined in the synthesis methods.

TABLE 1

| Ex. | $R^1$ | $R^2$ | $R^3$ | R | n | Het | Procedure |
|---|---|---|---|---|---|---|---|
| Examples of formula I where m = 0 and the other groups as described were prepared by the procedure below: | | | | | | | |
| 1 | methyl | methyl | methyl | — | 0 | 3-pyridyl | B |
| 2 | methyl | methyl | phenyl | — | 0 | 3-pyridyl | B |
| 3 | methyl | methyl | phenyl | — | 1 | 3-pyridyl | B |
| 4 | methyl | methyl | phenyl | — | 2 | 3-pyridyl | B |
| 5 | methyl | phenyl | phenyl | — | 0 | 3-pyridyl | B |
| 6 | methyl | phenyl | 4Clphenyl | — | 1 | 3-pyridyl | B |
| 7 | phenyl | phenyl | phenyl | — | 0 | 3-pyridyl | B |
| 8 | methyl | $CH=CH_2$ | phenyl | — | 0 | 3-pyridyl | B |
| 9 | methyl | phenyl | 3-pyridyl | — | 0 | 3-pyridyl | B |
| 10 | $OC_4H_8Cl$ | $CH=CH_2$ | phenyl | — | 0 | 3-pyridyl | B |
| 11 | methyl | methyl | methyl | — | 0 | 5-pyrimidinyl | A |
| 12 | methyl | methyl | phenyl | — | 2 | 5-pyrimidinyl | B |
| 13 | methyl | phenyl | phenyl | — | 0 | 5-pyrimidinyl | B |
| Examples of formula I where m = 1: | | | | | | | |
| 14 | methyl | methyl | methyl | H | 0 | 3-pyridyl | C |
| 15 | methyl | methyl | t-butyl | H | 0 | 3-pyridyl | C |
| 16 | ethyl | ethyl | ethyl | H | 0 | 3-pyridyl | C |
| 17 | methyl | methyl | phenyl | H | 0 | 3-pyridyl | C |
| 18 | methyl | phenyl | phenyl | H | 0 | 3-pyridyl | C |
| 19 | methyl | phenyl | 4Clphenyl | H | 1 | 3-pyridyl | C |
| 20 | methyl | phenyl | phenyl | H | 0 | pyrazinyl | C |
| 21 | methyl | methyl | methyl | $SiR^1R^2R^3$ | 0 | 3-pyridyl | C |
| 22 | methyl | methyl | phenyl | $SiR^1R^2R^3$ | 0 | 3-pyridyl | C |
| 23 | methyl | phenyl | phenyl | $SiR^1R^2R^3$ | 0 | 3-pyridyl | C |
| 24 | ethyl | ethyl | ethyl | $SiR^1R^2R^3$ | 0 | 3-pyridyl | C |
| Other examples of the present invention include, where m = 0 | | | | | | | |
| 25 | isopropyl | methyl | methyl | — | 0 | 3-pyridyl | |
| 26 | n-butyl | methyl | methyl | — | 0 | 3-pyridyl | |
| 27 | t-butyl | ethyl | ethyl | — | 0 | 3-pyridyl | |
| 28 | methyl | phenyl | 4Ephenyl | — | 1 | 3-pyridyl | |

TABLE 1-continued

| Ex. | R¹ | R² | R³ | R | n | Het | Procedure |
|---|---|---|---|---|---|---|---|
| 29 | methyl | phenyl | 4CF₃phenyl | — | 1 | 3-pyridyl | |
| 30 | methyl | 4Fphenyl | 4Fphenyl | — | 1 | 3-pyridyl | |
| 31 | methyl | phenyl | 4Clphenyl | — | 2 | 3-pyridyl | |
| 32 | ethyl | phenyl | 4Clphenyl | — | 2 | 3-pyridyl | |
| 33 | methyl | 4Fphenyl | 4Clphenyl | — | 2 | 3-pyridyl | |
| 34 | methyl | phenyl | 4Fphenyl | — | 2 | 3-pyridyl | |
| 35 | ethyl | phenyl | 4Fphenyl | — | 2 | 3-pyridyl | |
| 36 | methyl | 4Fphenyl | 4Fphenyl | — | 2 | 3-pyridyl | |
| 37 | methyl | CH=CH₂ | 4Clphenyl | — | 2 | 3-pyridyl | |
| 38 | methyl | 2Clphenyl | 4Clphenyl | — | 2 | 3-pyridyl | |
| 39 | CH₂=CH₂ | phenyl | 4Clphenyl | — | 1 | 3-pyridyl | |
| 40 | CH₂=CH₂ | phenyl | 4Clphenyl | — | 2 | 3-pyridyl | |
| 41 | CH₂=CH₂ | phenyl | 4Fphenyl | — | 1 | 3-pyridyl | |
| 42 | CH₂=CH₂ | phenyl | 4Fphenyl | — | 2 | 3-pyridyl | |
| 43 | methyl | phenyl | 4Clphenyl | — | 2 | 5-pyrimidinyl | |
| 44 | ethyl | phenyl | 4Clphenyl | — | 2 | 5-pyrimidinyl | |
| 45 | methyl | 4Fphenyl | 4Clphenyl | — | 2 | 5-pyrimidinyl | |
| 46 | methyl | phenyl | 4Fphenyl | — | 2 | 5-pyrimidinyl | |
| 48 | ethyl | phenyl | 4Fphenyl | — | 2 | 5-pyrimidinyl | |
| 49 | methyl | 4Fphenyl | 4Fphenyl | — | 2 | 5-pyrimidinyl | |
| 50 | methyl | CH₂=CH₂ | 4Clphenyl | — | 2 | 5-pyrimidinyl | |
| 51 | methyl | 2Clphenyl | 4Clphenyl | — | 2 | 5-pyrimidinyl | |
| 52 | methyl | 2Fphenyl | 4Clphenyl | — | 2 | 5-pyrimidinyl | |
| 53 | methyl | 2Clphenyl | 4Fphenyl | — | 2 | 5-pyrimidinyl | |
| 54 | methyl | 2Fphenyl | 4Fphenyl | — | 2 | 5-pyrimidinyl | |
| Other examples of the present invention include, where m = 1 | | | | | | | |
| 55 | isopropyl | methyl | methyl | H | 0 | 3-pyridyl | |
| 56 | n-butyl | methyl | methyl | H | 0 | 3-pyridyl | |
| 57 | t-butyl | ethyl | ethyl | H | 0 | 3-pyridyl | |
| 58 | methyl | phenyl | 4Fphenyl | H | 1 | 3-pyridyl | |
| 60 | methyl | 4Fphenyl | 4Fphenyl | H | 1 | 3-pyridyl | |
| 61 | methyl | phenyl | 4Clphenyl | H | 2 | 3-pyridyl | |
| 62 | ethyl | phenyl | 4Clphenyl | H | 2 | 3-pyridyl | |
| 63 | methyl | 4Fphenyl | 4Clphenyl | H | 2 | 3-pyridyl | |
| 64 | methyl | phenyl | 4Fphenyl | H | 2 | 3-pyridyl | |
| 65 | ethyl | phenyl | 4Fphenyl | H | 2 | 3-pyridyl | |
| 66 | methyl | 4Fphenyl | 4Fphenyl | H | 2 | 3-pyridyl | |
| 67 | methyl | CH₂=CH₂ | 4Clphenyl | H | 2 | 3-pyridyl | |
| 68 | methyl | 2Clphenyl | 4Clphenyl | H | 2 | 3-pyridyl | |

The elemental analysis and melting points for examples 1-24 are set forth in Table 2.

TABLE 2

| | Elemental Analysis/Melting Point | | | | | | | | |
|---|---|---|---|---|---|---|---|---|---|
| | Carbon | | Hydrogen | | Nitrogen | | Silicon | | |
| Example | Calc. | Found | Calc. | Found | Calc. | Found | Calc. | Found | M.P.(°C.) |
| 1 | 63.58 | 63.39 | 8.61 | 8.73 | 9.27 | 9.39 | 18.54 | 17.81 | Oil |
| 2 | 73.24 | 73.04 | 7.04 | 6.79 | 6.57 | 6.79 | 13.14 | 13.14 | Oil |
| 3 | 74.01 | 73.93 | 7.49 | 7.44 | 6.17 | 6.28 | 12.33 | 12.29 | Oil |
| 4 | 74.69 | 73.69 | 7.88 | 7.90 | 5.81 | 5.91 | 11.62 | 11.11 | Oil |
| 5 | 78.54 | 78.35 | 6.18 | 6.38 | 5.09 | 5.24 | 10.18 | 9.61 | 65-67 |
| 6 | 70.48 | 69.41 | 5.56 | 5.48 | 4.33 | 4.38 | 8.65 | 7.80 | Oil |
| 7 | 81.90 | 81.66 | 6.64 | 5.78 | 4.15 | 3.91 | 8.31 | 8.69 | 223-226 |
| 8 | 74.67 | 74.92 | 6.67 | 6.87 | 6.22 | 6.29 | 12.44 | 11.74 | Oil |
| 10 | 64.25 | 63.89 | 6.29 | 6.59 | 4.40 | 4.16 | 8.82 | 8.50 | Oil |
| 11 | 55.26 | 53.89 | 7.89 | 7.94 | 18.42 | 17.99 | 18.42 | 18.32 | Oil |
| 12 | 69.42 | 68.31 | 7.44 | 7.56 | 11.57 | 11.06 | 11.57 | 11.84 | Oil |
| 13 | 73.91 | 72.82 | 5.80 | 6.31 | 10.14 | 9.85 | 10.14 | 10.72 | Oil |
| 14 | 65.45 | 63.14 | 9.09 | 9.22 | 8.48 | 7.93 | 16.97 | 18.85 | Oil |
| 15 | 69.56 | 69.19 | 10.14 | 10.34 | 6.76 | 6.52 | 13.53 | 13.94 | Oil |
| 16 | 69.56 | 68.12 | 10.14 | 10.31 | 6.76 | 6.49 | 13.53 | 11.30 | 68-70 |
| 17 | 74.01 | 73.31 | 7.49 | 7.49 | 6.17 | 5.86 | 12.33 | 10.13 | Oil |
| 18 | 78.89 | 78.06 | 6.57 | 6.92 | 4.84 | 4.56 | 9.69 | 8.97 | Oil |
| 19 | 71.11 | 69.92 | 5.92 | 5.87 | 4.15 | 3.94 | 8.30 | 5.56 | Oil |
| 20 | 74.48 | 73.13 | 6.21 | 6.18 | 9.65 | 8.89 | 9.65 | 9.49 | Oil |
| 21 | 60.76 | 60.31 | 9.70 | 9.65 | 5.91 | 5.59 | 23.63 | 23.37 | Oil |
| 22 | 73.13 | 72.05 | 7.48 | 7.52 | 3.88 | 3.55 | 15.51 | 16.44 | Oil |
| 23 | 79.17 | 77.99 | 6.39 | 6.47 | 2.89 | 2.70 | 11.55 | 11.17 | Oil |
| 24 | 64.75 | 64.75 | 10.90 | 11.87 | 4.36 | 4.38 | 17.44 | 15.35 | Oil |

Chlorine analysis was completed for the following examples:

| Example | Calc. | Found |
|---|---|---|
| 6 | 60.76 | 60.31 |
| 10 | 11.18 | 11.37 |
| 19 | 10.52 | 10.67 |

The following Examples disclose the preparation of compounds of this invention.

EXAMPLE 2

Preparation of Example 3-(Dimethylphenylsilyl)pyridine Via Procedure B:

In a 1 liter, 4 neck round bottom flask stirring under $N_2$ was charged 80.6 milliliters (ml) of n-BuLi (1.55 Molar (M) solution, 0.125 moles, 1.25 equivalents (eq.)) to 300 ml of ether with stirring at $-78°$ C. To the reaction was added, dropwise, 15.8 grams (g) of 3-bromopyridine (0.10 moles, 1.0 eq.) in 100 ml of ether, over 20 minutes while maintaining the temperature between $-50°$ C. and $-70°$ C. After stirring for 20 minutes, 21.3 g of chlorodimethylphenylsilane (0.125 moles, 1.25 eq.) in 50 ml of ether was added dropwise maintaining the temperature below $-50°$ C. after which the reaction was allowed to come to ambient temperature. After 1 hour, gas liquid chromatography (GLC) indicated complete consumption of the silyl chloride. The reaction mixture was stirred overnight at room temperature. The reaction was quenched by adding 200 ml of water, and extracted with ether/ethyl acetate (200 ml/450 ml) and washed with water (2×200 ml). Drying and concentrating afforded 26.0 g of crude product of which 6.7 g was purified by flash chromatography with 3:7 ethyl acetate/hexane and afforded 2.1 g of an oil (31.2% yield based on the 6.7 g chromatographed portion).

Elemental Analysis: calculated for $C_{13}H_{15}NSi$

|  | C | H | N | Si |
|---|---|---|---|---|
| Theoritical: | 73.24 | 7.04 | 6.57 | 13.14 |
| Found: | 73.04 | 7.34 | 6.79 | 13.14 |

NMR (60 MHz) 0.6(s, 6H), 7.1–7.8 (m,7H), and 8.5–8.8 (m, 2H)

Preparation of Example 11: 5-(Trimethylsilyl)pyrimidine Via Procedure A:

In a 500 ml 4 neck round bottom flask stirring under $N_2$ was charged 1.2 g of Mg (0.050 moles, 1.0 eq) and 5.43 g of chlorotrimethylsilane (0.050 moles, 1.0 eq.) in 50 ml of HMPA (hexamethylphosphoramide) which was heated at 80° C. for 4 hours. To the reaction was added dropwise, 6.4 g of 5-bromopyrimidine (0.040 moles, 0.8 eq.) in 50 ml of HMPA while maintaining the temperature at 80° C. The reaction mixture was stirred for 18 hours at 75° C. after which GLC indicated complete consumption of the 5-bromopyrimidine. The reaction was quenched by adding 100 ml of water, acidified with 10% HCl and extracted with 2×250 ml of ethyl acetate (EtOAc). The acidic aqueous solution was neutralized with 6M NaOH to pH 10 and extracted with 250 ml of EtOAc. The extractions were combined and washed with 4×250 ml aliquots of distilled water. Drying and concentrating afforded 1.2 g of crude product which was purified by flash chromatography with 1:4 ethyl acetate/hexane and afforded 0.6 g of a clear oil (9.8% yield).

Elemental Analysis: calculated for $C_7H_{12}N_2Si$

|  | C | H | N | Si |
|---|---|---|---|---|
| Theoritical: | 55.26 | 7.89 | 18.42 | 18.42 |
| Found: | 53.89 | 7.84 | 17.99 | 18.32 |

NMR (60 MHz, $CDC_{13}$): 0.2–0.3 (s,9H), 8.6(s,2H) and 9.0(s,1H)

Preparation of Example 15: 3-(tert-Butyldimethylsilylmethyl)pyridine Via Procedure C:

In a 500 ml 3 neck round bottomed flask stirring under $N_2$ was charged 33.1 ml of 2M phenyl lithium, in 70/30 cyclohexane diethyl ether, (0.0662 moles, 1.0 eq.), to which 6.70 g of diisopropylamine (1.0 eq. 0.0662 moles) in 10 ml of diethylether was pipetted into the flask followed by rapid addition of 6.16 g of 3-picoline (1.0 eq., 0.066 moles) in 10 ml of diethylether and 10.0 g of tert-butyldimethylsilylchloride (1.0 eq., 0.0662 moles) in 10 ml diethyl ether. The temperature of the reaction was maintained below 35° C. with an ice bath during the additions. After 1 hour of stirring GLC indicated the reaction was complete. The reaction was quenched by adding 100 ml of water, extracted with 250 ml of diethylether and washed with 2×100 ml of water. The ether was dried over magnesium sulfate and concentrated to give 12.3 g of an orange oil. GLC indicated the crude mixture was 96% product. A 7.0 g portion was purified by flash chromatography with 1:4 ethyl acetate/hexane and afforded 3.8 g (48.7% yield based on chromatographic portion) of 3-(tert-butyldimethylsilyl)pyridine.

Elemental Analysis: calculated for $C_{12}H_{21}NSi$

|  | C | H | N | Si |
|---|---|---|---|---|
| Theor: | 69.56 | 10.14 | 6.76 | 13.53 |
| Found: | 69.19 | 10.34 | 6.52 | 13.94 |

NMR (60 MHz), $CDCl_3$) $-0.06$(s,6H), 1.0(s,9H), 2.1(s,2H), 6.9–7.4(m,2H)

Preparation of Exs. 18 and 23: 3-(diphenylmethylsilylmethyl)pyridine and 3-(bis-(diphenylmethylsilyl))methylpyridine Via Procedure C:

In a 250 ml 3 neck round bottom flask stirring under $N_2$ was charged 32.2 ml of 2M phenyl lithium, in 70/30 cyclohexane diethyl ether, (0.0644 moles, 1.0 eq.), to which 6.50 g of diisopropylamine (1.0 eq. 0.0662 moles) in 10 ml of diethylether was pipetted into the flask followed by rapid addition of 6.0 g of 3-picoline (1.0 eq., 0.044 moles) in 10 ml of diethylether and 15.0 g of chlorodiphenylmethylsilane (1.0 eq., 0.0644 moles) in 10 ml diethyl ether. The temperature of the reaction was maintained below 35° C. with an ice bath during the additions. After 1 hour of stirring GLC of an aliquot indicated two major products, a monosilylated product (GLC area percent of 27% ) and a disilylated product (GLC area percent of 41%). The reaction was quenched by adding 100 ml of water, extracted with 250 ml of diethylether from basic aqueous (pH10) and washed with 2×100 ml of water. The ether was dried over magnesium sulfate and concentrated to give 18.6 g of an orange oil. A 9.0 g portion was purified by flash chromatography with 1:4 ethyl acetate/hexane and afforded two products. The lower Rf product provided 0.8 g of an oil which solidified on standing and gave 0.7 g (mp. 68°–70° C.) of Example 18, 3-(diphenylmethylsilyl)pyridine (10% yield based on chromatographed portion). The higher Rf product, 1.4 g of a viscous oil (10.4% yield based on chromatographed portion), was identified as 3-(bis-(diphenylmethylsilyl)methyl)pyridine (Example 23).

Lower Rf product (Ex. 18):
Elemental Analysis: calculated for $C_{19}H_{19}NSi$

|  | C | H | N | Si |
|---|---|---|---|---|
| Theoretical: | 78.89 | 6.57 | 4.84 | 9.69 |
| Found: | 78.06 | 6.92 | 4.56 | 8.97 |

NMR (200 MHz), $CDCl_3$) 0.045(s,3H), 2.52(s,2H), 6.9–7.55(m, 12H) and 8.05–8.35 (m,2H)

Higher Rf product (Ex. 23):
Elemental Analysis: calculated for $C_{32}H_{31}NSi2$

|  | C | H | N | Si |
|---|---|---|---|---|
| Theoretical: | 79.17 | 6.39 | 2.89 | 11.55 |
| Found: | 77.99 | 6.47 | 2.70 | 11.17 |

NMR (200 MHz), $CDCl_3$) 0.045(s,6H), 2.85(s,1H), 6.9–7.55(m,22H) and 7.95–8.15 (m,2H)

In Vivo Fungicidal Testing

The compounds of this invention were tested for fungicidal activity in vivo against, rice blast (RB), tomato late blight (TLB wheat leaf rust (WLR), septoria leaf and glume blotch of wheat (SNW) and wheat powder mildew (WPM).

The compounds were dissolved in a 2:1:1 mixture of water, acetone, and methanol by weight, sprayed onto the plants and allowed to dry the plants were inoculated with the fungus after about 24 hours. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants) at a compound dose of 50, 100 or 200 parts per million.

Rice Blast (RB):

Two week old M201 rice plants were inoculated with $2.5 \times 10^5$ spores per pot of Magnaporthe grisea (Pyricularia oryzae) by spraying the leaves and stems with a DeVilbiss atomizer. The inoculated plants were incubated in a humid environment 80° F. for about 24 hours, then placed in a greenhouse environment (70° F. to 75° F.). Six to seven days after inoculation, the percent disease control was determined.

Tomato Late Blight (TLB):

Phytophthora infestans was cultured on V8 juice plus $CaCO_3$agar for three to four weeks. The spores were washed from the agar with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then removed to the controlled environment room (65–°70° F.) and after five days disease control levels were evaluated.

Wheat Leaf Rust (WLR)

Puccinia recondita (f. sp. tritici Races PKB and PLD) was cultured on seven day old wheat (cultivar Fielder) over a 14 day period in the greenhouse. Spores were collected from the leaves with a cyclone vacuum or by settling on aluminum foil (and stored or used fresh). A suspension was prepared by adding 20 milligrams (mg) (urediospores) per ml of Soltrol oil. The suspension was dispensed into gelatin capsules (0.7 ml capacity) which attach to the oil atomizers. One capsule is used per flat of twenty of the two inch square pots of seven day old Fielder wheat. Inoculated plants were placed in a mist cabinet at 68° F. for 24 hours. Disease control levels were evaluated eleven days after inoculation.

Wheat Powdery Mildew (WPM):

Erysiphe graminis (f. sp. tritici) was cultured on Hart wheat seedlings in a controlled temperature room at 65° F. to 75° F. Mildew spores were shaken from the culture plants onto Hart wheat seedlings which had been sprayed previously with the fungicidal compounds. The inoculated seedlings were kept in a controlled temperature room at 65° F. to 75° F. and subirrigated. The percent disease control was rated 8 to 10 days after inoculation.

Wheat Leaf Blotch (SNW):

Septoria nodorum was maintained on Czapek-Dox V-8 Juice agar plates in an incubator in the dark at 20° C. for 48–72 hours, then incubated at 20° C. with alternating periods of 12 hours of light and 12 hours of darkness. A water suspension of the spores was obtained by shaking the portion of the plate with fungal material in deionized water and filtering through cheesecloth. The spore-containing water suspension was diluted to a spore concentration of $3.0 \times 10^6$ per ml. The inoculum was dispersed by a DeVilbiss atomizer over one week old Fielder wheat plants which had been sprayed previously with the fungicide compound. The inoculated plants were placed in a humidity cabinet at 20° C. with alternating periods of 12 hours of light and 12 hours of darkness for 96 hours. The inoculated seedlings were then moved to a controlled environment room as above and scored after 8 more days of incubation. Disease control levels were recorded as percent control 10 days after inoculation and are reported in Table 3.

TABLE 3

| Cmpd. # | (% Control at 100 ppm) | | | | |
|---|---|---|---|---|---|
|  | RB | SNW | TLB | WLR | WPM |
| 1 | 0 | 80 | 0 | 0 | 50 |
| 2 | 0 |  | 0 | 0 | 85 |
| 3 | 100 |  | 50 | 50 | 50 |
| 4 | 0 | 50 | 100 | 75 | 80 |
| 5 | 80 | 50 | 100 | 0 | 95 |
| 6 | 99$^a$ |  | 0 | 80 | 100$^b$ |
| 7 | 0 |  | 0 | 50 | 0 |
| 8 | 0 | 0 | 90 | 0 | 80 |
| 9 | 0$^a$ |  | 0$^a$ | 50$^a$ | 85$^a$ |
| 10 | 80 |  | 0 | 95 | 95 |
| 11 | 0 | 0 | 0 | 0 | 0 |
| 12 | 0 |  | 0 | 0 | 0 |
| 13 | 0 | 0 | 0 | 85 | 100 |
| 14 | 0 | 0 | 0 | 50 | 85 |
| 15 | 0$^a$ |  | 0$^a$ | 0$^a$ | 99$^a$ |
| 16 | 0$^a$ |  | 0$^a$ | 0$^a$ | 85$^a$ |
| 17 | 0 |  | 0 | 0 | 0 |
| 18 | 0 |  | 80 | 0 | 85 |
| 19 | 0$^a$ |  | 0$^a$ | 0$^a$ | 99$^a$ |
| 20 | 0 | 0 | 0 | 0 | 75 |
| 21 | 0 | 50 | 0 | 80 | 50 |
| 22 | 0 |  | 0 | 50 | 85 |
| 23 | 0 |  | 0 | 0 | 0 |

TABLE 3-continued

| Cmpd. # | (% Control at 100 ppm) | | | | |
|---|---|---|---|---|---|
|  | RB | SNW | TLB | WLR | WPM |
| 24 | 0 |  | 0 | 0 | 85 |

*a*At 200 ppm;
*b*At 50 ppm

In Vitro Fungicidal Testing

Compounds of this invention were tested in a microtiter plate assay for fungicidal activity against a variety of fungi over a range of different doses. The following oganisms were employed in the test *Pythium ultimum* (PYU), *Piricularia oryzae* (PIR), *Botrytis cinerea* (BOC), *Fusarium roseum* (FUS), *Rhizoctonia solani* (RHI), *Cochliobulus sativus* (HEL), *Alternaria solani* (ALT), *Ustilago maydis* (UST), and *Xanthomonas campestris* (XAN).

All 8 fungi and the bacterium were transferred and maintained on potato dextrose agar (PDA) plates. To prepare inoculum, PYU was grown in asparagine-sucrose broth (ASB) shake culture and FUS, XAN and RHI were grown in a yeast-dextrose broth (YDB) on a shaker. Culture flasks were inoculated with 6 mycelial plugs (except for PYU which was inocluated with only 3 plugs) taken from PDA plates. After two days growth the cultures were homogenized and diluted into fresh ASB (PYU) or YDB (FUS, XAN and RHI). Inoculum of PIR, BOC, HEL, UST, and ALT were prepared by lightly scraping conidia from the surface of cultures grown on PDA into YDB. The conidial suspensions were strained through a double layer of sterile cheesecloth to remove any mycelial clumps. Ten milliliters of the culture solutions of RHI, FUS and XAN were added to 90 ml of YDB and 2 ml of the culture solution of PYU was added to 98 ml ASB. The various inoculum preparations were added in 175 microliter (μl) aliquots to wells of 96-well microtiter plates with 2 replicates per treatment. Test compounds were dissolved in acetone/methanol (1:1) at a concentration of 10 mg/ml, then 40 μl of the solution was added to 210 μl of sterile water to give 1600 ppm solution.

Aliquots (25 μl) of each solution were added to the inoculum in the microtiter plates to give a concentration of 200 ppm. The remaining doses of 100, 40 and 20 ppm were prepared by adjusting the aliquot of each solution in the required inoculum volume. Microtiter plates were incubated for 3 days at room temperature and fungal growth recorded as % control by comparison with control wells without test compound.

The results (expressed as inhibition of fungal growth) of the testing are in Table 4.

TABLE 4

| Cmpd. | Dose | Invitro Results - % Control | | | | | | | | |
|---|---|---|---|---|---|---|---|---|---|---|
|  |  | ALT | BOC | FUS | HEL | PIR | PYU | RHI | UST | XAN |
| 1 | 100 | 50 | 0 | 0 | 0 | 0 | 0 | 0 | 0 | 0 |
| 2 | 100 | 90 | 100 | 100 | 100 | 100 | 100 | 90 | 0 | 0 |
|  | 20 | 0 | 0 | 50 | 75 | 0 | 0 | 0 | 0 | 0 |
| 5 | 100 | 90 | 100 | 100 | 100 | 100 | 0 | 100 | 0 | 0 |
|  | 20 | 75 | 95 | 50 | 100 | 100 | 0 | 50 | 0 | 0 |
| 6 | 200 | 95 | 100 | 0 | 100 | 100 | 50 |  | 100 | 0 |
|  | 40 | 90 | 100 | 0 | 100 | 100 | 0 |  | 100 | 0 |
| 6 | 100 | 90 | 100 | 50 | 100 | 100 | 0 | 100 | 0 | 0 |
|  | 20 | 90 | 100 | 0 | 100 | 100 | 0 | 100 | 0 | 0 |
| 9 | 200 | 95 | 100 | 100 | 100 | 100 | 100 |  | 100 | 0 |
|  | 40 | 75 | 100 | 30 | 100 | 100 | 0 |  | 100 | 0 |
| 11 | 100 | 0 | 0 | 0 | 50 | 0 | 0 | 0 | 0 | 0 |
|  | 20 | 0 | 0 | 0 | 0 | 0 | 0 | 0 | 0 | 0 |
| 13 | 100 | 75 | 0 | 90 | 90 | 100 | 100 | 100 | 50 | 0 |
|  | 20 | 0 | 0 | 50 | 50 | 100 | 0 | 0 | 0 | 0 |
| 14 | 100 | 0 | 0 | 0 | 0 | 0 | 0 | 0 | 0 | 0 |
| 16 | 200 | 0 | 75 | 50 | 100 | 100 | 0 |  | 0 | 0 |
|  | 40 | 0 | 75 | 50 | 90 | 100 | 0 |  | 0 | 0 |
| 17 | 100 | 95 | 100 | 100 | 100 | 100 | 75 | 100 | 0 | 50 |
|  | 20 | 50 | 50 | 50 | 75 | 95 | 0 | 0 | 0 | 0 |
| 18 | 100 | 75 | 95 | 100 | 95 | 100 | 100 | 100 | 0 | 0 |
|  | 20 | 50 | 75 | 50 | 0 | 100 | 100 | 50 | 0 | 0 |
| 19 | 100 | 75 | 75 | 75 | 100 | 100 | 0 | 50 | 0 | 0 |
|  | 20 | 75 | 50 | 50 | 100 | 100 | 0 | 0 | 0 | 0 |
| 20 | 100 | 50 | 75 | 75 | 50 | 90 | 100 | 100 | 0 | 0 |
|  | 20 | 0 | 0 | 50 | 0 | 75 | 0 | 0 | 0 | 0 |
| 21 | 25 | 0 | 0 | 0 | 0 | 0 |  | 0 | 0 | 0 |
| 24 | 200 | 0 | 0 | 0 | 75 | 100 | 100 |  | 0 | 0 |
|  | 40 | 0 | 0 | 0 | 0 | 75 | 100 |  | 0 | 0 |

The silyl heterocycles, enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Co., Ridgewood, N.J.

In general, the compounds of this invention can be dissolved in certain solvents such as acetone, methanol, ethanol, dimethylformamide, pyridine or dimethyl sulfoxide and such solutions can be extended with water.

The concentrations of the solution can vary from about 1% to about 90% with a preferred range being from about 5% to about 50% by weight fungicide.

For the preparation of emulsifiable concentrates, the compound can be dissolved in suitable organic solvents, or a mixture of solvents, together with an emulsifying agent with permits dispersion of the fungicide in water. The concentration of the active ingredient in emulsifiable concentrates is usually from about 10% to about 90% and in flowable emulsion concentrates, this can be as high as about 75% by weight.

Wettable powders suitable for spraying can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range from about 20% to about 98%, preferably from about 40% to about 75% by weight.

A water dispersible granular product may be obtained by granulating or agglomerating a suitable wettable powder formulation that is compatible with the active ingredients. Agglomeration may be carried out by any convention method such as pan agglomeration. Illustrative water dispersible granules are described in U.S. Pat. No. 3,954,439.

Dusts are prepared by mixing the silyl heterocycles, enantiomorphs, salts and complexes thereof with finely divided inert solids which can be organic or inorganic in nature. Materials useful for this purpose include botanical flours, silicas, silicates, carbonates and clays. On convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The silyl heterocyclic compounds, enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 pound to about 50 pounds per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 pounds per acre. As a foliar fungicide, the toxicant is usually applied to growing plants at a rate of from about 0.25 to about 10 pounds per acre.

Fungicides which can be combined with the fungicides of this invention include but are not limited to:

(a) dithiocarbamate and derivatives such as: ferbam, ziram, maneb, mancozeb, zineb metham, thiram, the complex of zineb and polyethylene thiuram disulfide, dazomet; and mixtures of these and mixtures with copper salts;

(b) nitrophenol derivatives such as: dinocap binapacryl, and isopropyl carbonate;

(c) heterocyclic structures such as: captan, forpet, glyodine, anilazine, ditalimfos, etradiazole, dithianon, thioquinox, benomyl, thiabendazole, triarimol, cycloheximide, captafol, ethirimol, dodemorph, vinclozolin, quinomethionate, iprodione, procymidone, triadimenol, triadimefon, bitertanol, prochloraz, fenarimol, fiutriafol, flusilazole, propiconazole, myclobutanil, fenbuconazole, hexaconazole, cyproconazole, tebuconazole, diniconazole, difenoconazole, epoxiconazole, metconazole, fluquinconazole, tetraconazole, bromuconazole, ICI5504A, BAS490F, fenpropimorph, fenpropidine, dodemorph, and triforine;

(d) miscellaneous halogenated fungicides such as: chloranil, dichlone, chloroneb, tricamba, TCPN, dichloran, and PCNB;

(e) fungicidal antibiotics such as: griseofulvin, kasugamycin, streptomycin, polyoxin, and validamycin;

(f) copper-based fungicides such as: cuprous oxide, basic cupric chloride, basic copper carbonate, copper naphthenate, and Bordeaux mixture; and (g) miscellaneous fungicides such as: dodine, phenylmercuric acetate, thiophanatemethyl.

The silyl heterocycles, enantiomorphs, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit and nut orchards, vegetables and golf course applications. Other applications of the compounds of this invention will suggest themselves to those with skill in the art.

The compounds of the present invention have fungitoxic activity, providing control of a broad spectrum of phytopathogenic fungi including those in the classes of Deuteromycetes (Fungi Imperfecti), Oomycetes, Basidiomycetes and Ascomycetes. More particularly, the method of this invention provides for control of organisms which cause diseases on many crops including such important genera as Erysiphe, Puccinia, Leptoshaeria, Thanatephorus, Pyricularia, Phytophthora, Plasmopara, Alternaria, Guignardia, Pseudocercosporella, Venturia, Monilinia, and Ustilago. More particularly, wheat diseases including powdery mildew (Erysiphe graminis), leaf rust (Puccinia recondita), stem rust (Puccinia graminis f.sp. tritici) and septoria leaf and glume blotch (Leptosphaeria nodorum) are controlled by the method of the invention. Other diseases controlled include cercospora leaf spots (Mycosphaerella arachidis and Cercospora beticola), botrytis diseases (Botryotinia fuckelioniana), helminthosporium diseases (Cochliobolous miyabeanus, Cochliobolous sativus, Cochliobolus heterostrophus), rice blast (Magnaporthe grisea) and alteraria blight (Alternaria solani). Consequently, various compounds of this invention may be useful in treating fungi which may affect cereal, fruit, nut, vegetable, feed and fiber crops.

Although the invention has been described with regard to its preferred embodiments which constitute the best mode presently known to the inventors, it should be understood that various changes and modifications as would be obvious to one having ordinary skill in this art may be made without departing from the scope of the invention which is set forth in the following claims.

We claim:

1. A compound of the formula

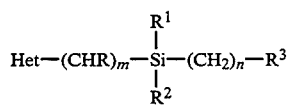

wherein Het is a six membered aromatic heterocyclic ring selected from 2-pyridyl, 3-pyridyl, 4-pyridyl, 2-pyrimidyl, 4-pyrimidyl, 5-pyrimidyl, pyrazinyl, 3-pyridazinyl and 4-pyridazinyl; R is H or

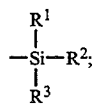

$R^1$, $R^2$ and $R^3$ are independently selected from the group consisting of ($C_1$-$C_6$) alkyl, ($C_2$-$C_6$) alkenyl, ($C_2$-$C_6$) alkynyl, ($C_1$-$C_6$) alkoxy, phenyl, benzyl and phenethyl each of which may be optionally substituted with up to three substituents wherein the substituents may be independently selected from the group consisting of ($C_1$-$C_6$)alkyl, ($C_2$-$C_6$) alkenyl, ($C_2$-$C_6$) alkynyl, ($C_1$-$C_6$) alkoxy, halo and cyano; m is 0 or 1 and n is zero, one or two;

provided that when Het is pyridine, m and n is zero .or one, and R is hydrogen, $R^1$, $R^2$ and $R^3$ are not methyl; and when $R^1$ is ($C_1$-$C_6$)alkyl or $CH=CH_2$, $R^2$ and $R^3$ are methyl or optionally substituted phenyl and. $m=n=0$, Het is not pyrimidine; and the agronomically acceptable enantiomorphs, acid addition salts and metal complexes thereof.

2. The compound of claim 1 wherein =0, n is 0, Het is 3-pyridyl; $R^1$ and $R^2$ are independently selected from ($C_2$-$C_6$)alkenyl and substituted ($C_1$-$C_6$)alkoxy; and $R^3$ is substituted phenyl.

3. The compound of claim 2 wherein $R^1$ and $R^2$ are independently selected from the group consisting of vinyl and halo ($C_1$-$C_6$)alkoxy.

4. The compound of claim 1 wherein n is 1 and Het is 3-pyridyl.

5. The compound of claim 4 wherein $R^1$ and $R^2$ are independently selected from the group consisting of ($C_1$-$C_6$)alkyl, ($C_2$-$C_6$)alkenyl, halo-substituted ($C_1$-$C_6$)alkoxy and phenyl.

6. The compound of claim 5 wherein $R^3$ is substituted phenyl.

7. The compound of claim 4 wherein $R^1$ is alkyl and $R^2$ and $R^3$ are substituted phenyl.

8. The compound of claim 1 wherein m is 0, n is 2, $R^1$ is alkyl, $R^2$ and $R^3$ are substituted phenyl and Het is 3-pyridyl.

9. The compound of claim I wherein m is 0, n is 1, $R^1$ and $R^2$ are methyl, $R^3$ is phenyl and Het is 3-pyridyl.

10. The compound of claim 1 wherein m is 0, n is 1, $R^1$ is methyl, $R^2$ is phenyl, $R^3$ is 4-chlorophenyl and Het is 3-pyridyl.

11. The compound of claim 1 wherein Het is 5-pyrimidine.

12. The compound of claim 1 wherein m is 1, $R^1$ and $R^2$ are selected from the group consisting of substituted phenyl, alkyl, or substituted phenyl; $R^3$ is phenyl; and Het is 3-pyridyl.

13. A method of controlling phytotopathogenic fungus which comprising applying to the fungus or its habitat a fungicidally-effective amount of the compound of the formula

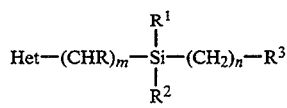

wherein Het is a six membered aromatic heterocyclic ring selected from 2-pyridyl, 3-pyridyl, 4-pyridyl, 2-pyrimidyl, 4-pyrimidyl, 5-pyrimidyl, pyrazinyl, 3-pvyridazinyl and 4-pyridazinyl; R is H or

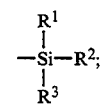

$R^1$, $R^2$ and $R^3$ are independently selected from the group consisting of ($C_1$-$C_6$) alkyl, ($C_2$-$C_6$) alkenyl, ($C_2$-$C_6$) alkynyl, ($C_1$-$C_6$) alkoxy, phenyl, benzyl and phenethyl each of which may be optionally substituted with up to three substituents wherein the substituents may be independently selected from the group consisting of ($C_1$-$C_6$) alkyl, ($C_2$-$C_6$) alkenyl, ($C_2$-$C_6$) alkynyl, ($C_1$-$C_6$) alkoxy, halo and cyano; m is 0 or 1 and n is zero, one or two;

provided that when Het is pyridine, m and n is zero or one, and R is hydrogen, $R^1$, $R^2$ and $R^3$ are not methyl; and when $R^1$ is ($C_1$-$C_6$)alkyl or $CH=CH_2$, $R_2$ and $R_3$ are methyl or optionally substituted phenyl and $m=n=0$, Het is not pyrimidine; and the agronomically acceptable enantiomorphs, acid addition sales and metal complexes thereof.

14. The method of claim 13 in which the compound is applied in the amount from about 0.1 to about 50 pounds per acre.

15. The method of claim 13 wherein the compound is applied to seeds at a level of from about 0.1 to about 20 ounces per 100 pound of seeds.

16. A compound having the formula:

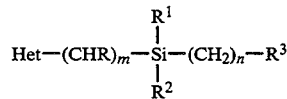

wherein m and n are O;
$R^1$ is methyl;
$R^2$ is phenyl;
$R^3$ is 3-pyridyl and
Het is 3-pyridyl.

* * * * *